United States Patent
Janik et al.

(10) Patent No.: US 7,274,440 B1
(45) Date of Patent: Sep. 25, 2007

(54) SYSTEMS AND METHODS FOR MEASURING STRESS IN A SPECIMEN

(75) Inventors: Gary Janik, Palo Alto, CA (US); Shankar Krishnan, Santa Clara, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 232 days.

(21) Appl. No.: 10/936,019

(22) Filed: Sep. 8, 2004

(51) Int. Cl.
*G01B 11/16* (2006.01)
*G01J 4/00* (2006.01)

(52) U.S. Cl. ............... 356/34; 356/33; 356/365
(58) Field of Classification Search ............ None
See application file for complete search history.

(56) References Cited

U.S. PATENT DOCUMENTS

| | | | | |
|---|---|---|---|---|
| 5,517,312 A | * | 5/1996 | Finarov | 356/630 |
| 5,764,365 A | * | 6/1998 | Finarov | 356/630 |
| 5,831,733 A | * | 11/1998 | de Groot | 356/369 |
| 5,844,684 A | * | 12/1998 | Maris et al. | 356/432 |
| 5,959,735 A | * | 9/1999 | Maris et al. | 356/632 |
| 5,979,244 A | * | 11/1999 | Michaelis | 73/800 |
| 6,208,421 B1 | * | 3/2001 | Maris et al. | 356/432 |
| 6,400,449 B2 | * | 6/2002 | Maris et al. | 356/72 |
| 6,590,656 B2 | * | 7/2003 | Xu et al. | 356/369 |
| 6,608,689 B1 | * | 8/2003 | Wei et al. | 356/630 |

(Continued)

OTHER PUBLICATIONS

Colbourne and Cassidy, Imaging of stress in GaAs diode lasers using polarization-resolved photoluminescence, IEEE J. Quantum Electronics, vol. 29, No. 1, pp. 62-68, 1993.*

(Continued)

*Primary Examiner*—Gregory J. Toatley, Jr.
*Assistant Examiner*—Jonathan Skovholt
(74) *Attorney, Agent, or Firm*—Baker & McKenzie LLP

(57) ABSTRACT

Systems and methods for measuring stress in a specimen are provided. One system includes an optical subsystem configured to measure stress-induced birefringence in patterned structures formed on the specimen. In some embodiments, the optical subsystem may be configured as a spectroscopic ellipsometer, a multi-angle laser ellipsometer, a polarimeter, a polarized reflectometer, or some combination thereof. The system also includes a processor coupled to the optical subsystem. The processor is configured to determine stress in a material of the patterned structures using the stress-induced birefringence measurements. One method includes measuring stress-induced birefringence in patterned structures formed on the specimen using an optical technique. The method also includes determining stress in a material of the patterned structures using the stress-induced birefringence measurements.

25 Claims, 4 Drawing Sheets

U.S. PATENT DOCUMENTS

| | | | |
|---|---|---|---|
| 6,611,330 B2 * | 8/2003 | Lee et al. | 356/369 |
| 6,650,405 B2 * | 11/2003 | Lam et al. | 356/33 |
| 6,657,736 B1 * | 12/2003 | Finarov et al. | 356/625 |
| 6,665,059 B2 * | 12/2003 | Kanno et al. | 356/33 |
| 6,713,753 B1 * | 3/2004 | Rovira et al. | 250/225 |
| 6,784,991 B2 * | 8/2004 | Rotter et al. | 356/369 |
| 6,798,512 B2 * | 9/2004 | Ebert et al. | 356/369 |
| 6,829,049 B1 * | 12/2004 | Uhrich et al. | 356/369 |
| 7,095,511 B2 * | 8/2006 | Chalmers et al. | 356/630 |
| 2003/0081196 A1 * | 5/2003 | Geiler et al. | 356/33 |
| 2003/0117626 A1 * | 6/2003 | Wei | 356/369 |
| 2003/0210394 A1 * | 11/2003 | Wei | 356/369 |
| 2004/0008349 A1 * | 1/2004 | Norton | 356/369 |
| 2004/0036876 A1 * | 2/2004 | Davis et al. | 356/367 |
| 2004/0109173 A1 * | 6/2004 | Finarov et al. | 356/625 |
| 2004/0114142 A1 * | 6/2004 | Wang | 356/365 |
| 2004/0125375 A1 * | 7/2004 | Some | 356/369 |
| 2004/0179199 A1 * | 9/2004 | Wei | 356/369 |
| 2004/0233436 A1 * | 11/2004 | Wang et al. | 356/369 |
| 2005/0046842 A1 * | 3/2005 | Uhrich et al. | 356/369 |
| 2005/0057755 A1 * | 3/2005 | Johnson et al. | 356/446 |

OTHER PUBLICATIONS

Mukerjee and Venkataraman, Characterization of strain in SiGe films using multiple angle of incidence ellipsometry, Appl. Phys. Lett., vol. 77, No. 22, pp. 3529-3531, 2000.*

Almashary and Kim, Analysis of stress in GaAs waveguides integrated with ZnO thinn films, SPIE vol. 2693, pp. 512-522, 1996.*

Vedam, "Applications of Polarized Light in Materials Research," SPIE vol. 88, 1976, pp. 78-83.

* cited by examiner

SYSTEMS AND METHODS FOR MEASURING STRESS IN A SPECIMEN

BACKGROUND OF THE INVENTION

1. Field of the Invention

The present invention generally relates to systems and methods for measuring stress in a specimen. Certain embodiments relate to methods that include determining stress in patterned structures on a specimen using stress-induced birefringence measurements of the patterned structures.

2. Description of the Related Art

The following description and examples are not admitted to be prior art by virtue of their inclusion in this section.

Fabricating semiconductor devices such as logic and memory devices typically includes processing a substrate such as a semiconductor wafer using a number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polish, etch, deposition, and ion implantation. Multiple semiconductor devices may be fabricated in an arrangement on a semiconductor wafer and then separated into individual semiconductor devices.

Semiconductor manufacturing involves fabricating semiconductor devices with many different materials. When dissimilar materials are formed in contact with one another, the materials may exhibit increased stress. For example, when a dielectric thin film is formed on a monocrystalline silicon substrate, stress may be produced in both the dielectric thin film and the monocrystalline silicon substrate. If the stress in either the thin film or the substrate becomes too high, then the thin film and/or the substrate may be damaged. For instance, the thin film may crack and pull away from the wafer thereby necessitating removal and re-formation of the thin film on the substrate. In another example, the substrate may become so warped that it is no longer viable for use in manufacturing semiconductor devices. For example, wafers that are warped may be unsuitable for lithography processes since the focus of the exposure tool will vary across the wafer due to the differences in the position of the uppermost surface of the wafer caused by the warping.

One example of a measurement device that can be used to measure stress in thin films is illustrated in U.S. Pat. No. 6,608,689 to Wei et al., which is incorporated by reference as if fully set forth herein. The systems described in this patent use a bow and warp measurement module to determine the level of stress in a thin film. The bow and warp measurement module measures stress using probe beam displacement information. For example, the amount and direction of the displacement of the probe beam on the detector provides a measure of the wafer local slope. The results of this measurement can be supplied as a known parameter (i.e., level of birefringence) to subsequent determination of the characteristics of the thin film. Therefore, by utilizing a determination of stress (from a measurement of angular displacement of the wafer), the calculations for thin film parameters (e.g., index of refraction n, extinction coefficient k, and thickness t) can be optimized using these measurements. In a similar manner, the system described in this patent can be used to correct stress measurements that are performed as described above using optical measurements of the thin film characteristics. For instance, the bow and warp stress measurements may be corrected for the actual thickness of the thin film formed on the substrate instead of using an assumed thickness value.

Although the systems described by Wei et al. may be useful for measuring stress and other parameters of thin films, these systems do have some limitations. For instance, these systems are not suitable for measuring stress in patterned structures formed on a wafer. In particular, the bow and warp measurements may not represent the stress on patterned structures since the bow and warp measurements are performed across a relatively large area of the wafer and therefore may not accurately reflect the stress proximate the patterned structures. In addition, the patterned structures may not cause a measurable change in the wafer local slope that is measured by the systems described by Wei et al. Therefore, the wafer local slope measurements are not accurate measurements of the stress in the patterned structures. Furthermore, the patterned structures may be formed on or within a material formed on the wafer. As such, a material may be interposed between the patterned structures and the wafer. As a result, any bow and warp measurements would produce measurements of stress caused by the combination of the patterned structures and any other materials present on the wafer. Consequently, these measurements will not accurately reflect the stress that is present in the patterned structures.

Measurement of stress in patterned structures on a wafer, however, is becoming increasingly important. For example, semiconductor patterned areas made of dissimilar materials can develop high levels of stress. These stress levels can degrade both performance and reliability. Two areas where stress is of particular importance are shallow trench isolation (STI) and copper interconnect. In STI, the silicon has submicron wide trenches etched within it, which are filled with silicon dioxide and/or silicon nitride. High levels of stress caused by the dissimilar materials can affect the electrical performance of the transistor and can even lead to cracking in the corners of the trenches. Copper interconnect structures include submicron trenches and round holes etched in dielectric materials such as silicon dioxides and low-k dielectrics. These trenches and holes are filled with copper for connecting transistors to each other to form a circuit. Again, stress can build up and cause problems such as void formation in the copper, even leading to complete breaks in the copper lines thereby forming opening circuits.

Some methods are available for measuring stress in patterned structures. One example of a method for measuring stress in a material is to perform x-ray diffraction (XRD) on a crystalline material in an array of structures on a wafer. Stress will change the spacing between atoms in the crystal, and this change in spacing can be measured with XRD. Another method is to perform Raman spectroscopy on silicon in the array of structures. The phonon spectrum of silicon is changed by stress, and this change in the phonon spectrum can be measured by Raman spectroscopy.

There are, however, several disadvantages to the above-described methods. For example, x-ray diffraction can only be performed on crystalline and polycrystalline materials. This excludes amorphous materials like silicon dioxide and low-k dielectric materials used in semiconductor interconnect structures, which is one area where stress measurement is of particular interest. Crystalline silicon is the only material used in conventional semiconductors where Raman spectroscopy can measure the phonon spectrum. Therefore, XRD and Raman spectroscopy are limited in the types of materials that they can measure. In addition, both XRD and Raman spectroscopy suffer from poor signal-to-noise ratios, and extended integration times are necessary to collect adequate signal levels. These long integration times force the throughput of the measurement systems to be relatively low.

Accordingly, it may be advantageous to develop systems and methods for measuring stress in patterned structures on a specimen that are flexible in the types of materials that can be measured and have sufficient signal-to-noise ratios, throughput, and accuracy.

SUMMARY OF THE INVENTION

An embodiment of the invention relates to a system configured to measure stress in a specimen. The system includes an optical subsystem configured to measure stress-induced birefringence in patterned structures formed on the specimen. The system also includes a processor coupled to the optical subsystem. The processor is configured to determine stress in a material of the patterned structures using the stress-induced birefringence measurements.

In some embodiments, the optical subsystem may be configured as a spectroscopic ellipsometer, a multi-angle laser ellipsometer, a polarimeter, a polarized reflectometer, or some combination thereof. In additional embodiments, the optical subsystem may include one or more such optical subsystems in combination with any other metrology and/or inspection subsystem known in the art (e.g., optical and/or non-optical subsystems configured for metrology and/or inspection). In one embodiment, the optical subsystem may be configured to measure the stress-induced birefringence at one or more infrared wavelengths.

In an embodiment, the patterned structures may include trenches filled with a dielectric material. In an alternative embodiment, the patterned structures may include copper interconnect structures. Preferably, the material of the patterned structures is at least partially transparent to at least one wavelength of light of the optical subsystem.

In another embodiment, the processor may also be configured to determine one or more geometrical parameters of the patterned structures using output generated by the optical subsystem. In one such embodiment, the processor may be further configured to determine the one or more geometrical parameters and the stress substantially simultaneously using a model describing effects of variations in the one or more geometrical parameters and the stress on polarization change in light detected by the optical subsystem.

In another embodiment, the processor may be configured to monitor one or more processes used to fabricate the patterned structures. In some embodiments, the processor may also be configured to control one or more processes used to fabricate the patterned structures using, for example, a feedback control technique. In additional embodiments, the processor may be configured to control one or more processes that will be used to fabricate the specimen using, for example, a feedforward control technique. The one or more processes may include front end of line (FEOL) processes or back end of line (BEOL) processes.

In some embodiments, the stress may be an average stress in the material of more than one of the patterned structures. In a different embodiment, the stress may include a stress distribution in the material. In such an embodiment, the processor may be configured to determine the stress distribution in the material using the stress-induced birefringence measurements and a finite element modeling method. Each of the embodiments of the system described above may be further configured as described herein.

Another embodiment relates to a different system that is configured to measure stress in a specimen. Like the system described above, this embodiment includes an optical subsystem configured to measure stress-induced birefringence in patterned structures formed on the specimen. However, unlike the system described above, this embodiment includes program instructions. The program instructions are executable on a processor to determine stress in a material of the patterned structures using the stress-induced birefringence measurements. This embodiment may be further configured as described herein. For example, the program instructions may be further executable on the processor to perform other functions of the processor described above.

An additional embodiment relates to a method for measuring stress in a specimen. This method includes measuring stress-induced birefringence in patterned structures formed on the specimen using an optical technique. The method also includes determining stress in a material of the patterned structures using the stress-induced birefringence measurements.

In some embodiments, the optical technique may include spectroscopic ellipsometry, multi-angle laser ellipsometry, polarimetry, polarized reflectometry, or some combination thereof. In some such embodiments, the method may also include performing other measurements of the patterned structures and/or the specimen using the optical technique, another optical technique, and/or a non-optical technique (e.g., an e-beam technique). In additional embodiments, measuring the stress-induced birefringence may include measuring the stress-induced birefringence at one or more infrared wavelengths.

In one embodiment, the patterned structures may include trenches filled with a dielectric material. In an alternative embodiment, the patterned structures may include copper interconnect structures. Preferably, the material of the patterned structures is at least partially transparent to at least one wavelength of light used by the optical technique.

In another embodiment, the method may also include determining one or more geometrical parameters of the patterned structures using output generated by the optical technique. In one such embodiment, determining the stress may include determining the one or more geometrical parameters and the stress substantially simultaneously using a model describing effects of variations in the one or more geometrical parameters and the stress on polarization change in light used by the optical technique.

In another embodiment, the method may include monitoring one or more processes used to fabricate the patterned structures. In a further embodiment, the method may include controlling one or more processes used to fabricate the patterned structures using, for example, a feedback control technique. In an additional embodiment, the method may include controlling one or more processes that will be used to fabricate the specimen using, for example, a feedforward control technique. The one or more processes may include FEOL processes or BEOL processes.

In some embodiments, the stress may be an average stress in the material of more than one of the patterned structures. In different embodiments, the stress may be a stress distribution in the material. In such embodiments, determining the stress may include determining the stress distribution in the material using the stress-induced birefringence measurements and a finite element modeling method. Each of the embodiments of the method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
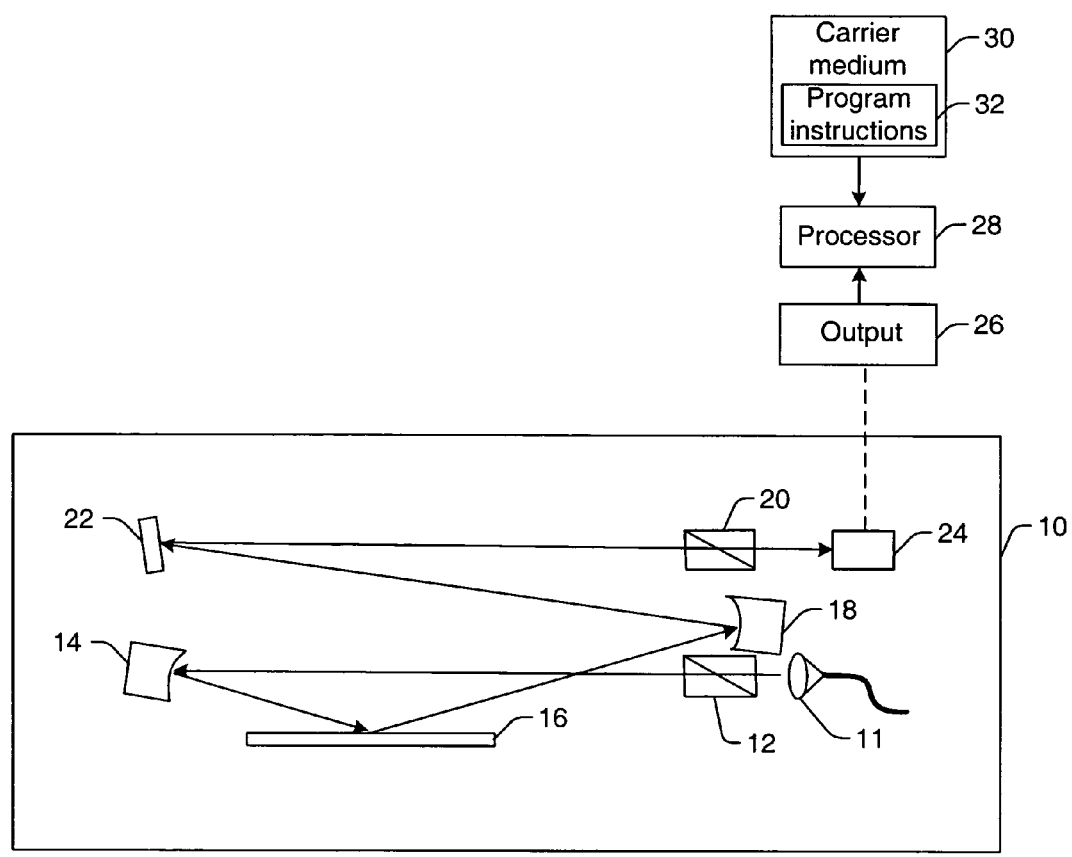
FIGS. 1-3 are schematic diagrams illustrating side views of different embodiments of a system configured to measure stress of a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" is generally defined as a wafer. The term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers formed upon a substrate. For example, such layers may include, but are not limited to, a resist, a dielectric material, and a conductive material. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer. Furthermore, although embodiments may be described herein with reference to a wafer, it is to be understood that the embodiments described herein may be used to measure stress in any other specimen known in the art.

As discussed further above, semiconductor patterned areas made of dissimilar materials can develop high levels of stress. These stress levels can degrade both performance and reliability. For example, the stress levels can result in cracking of structures and voids in structures that can lead to breaks in the structures. As such, the degradation of the device structures can reduce the electrical performance of the transistors or integrated circuits and can produce open circuits in the integrated circuits. Therefore, patterned structures are the most desirable location to measure stress (instead of, for instance, thin films) since the most undesirable effects of stress on semiconductor devices tend to show up in the patterned structures.

The systems and methods described herein can be used to measure the stress in patterned structures on a specimen such as a wafer. In general, the systems described herein include an optical subsystem that is configured to measure stress-induced birefringence in patterned structures formed on the specimen. As is known in the art, the term "birefringence" can be generally defined as a measure of the difference in the index of refraction of a material for different directions of light polarization, for a particular direction of light propagation. In other words, if a material has the same index of refraction for polarizations oriented in all directions, then that material does not exhibit birefringence. Thus, birefringence, B, can be defined by the following equation: $B=|n_{high}-n_{low}|$, where $n_{high}$ is the largest refractive index, and $n_{low}$ is the smallest refractive index in a material for a particular direction of light propagation. Materials that do not normally exhibit birefringence such as non-crystalline materials may exhibit birefringence when stressed. As such, the presence of birefringence in a material may provide an indication of the stress in that material. In particular, the optical subsystems described herein are configured to measure change in polarization of light reflected from patterned structures on a specimen, which as discussed further below is due, at least in part, to stress-induced birefringence in the patterned structures.

Figure 2:
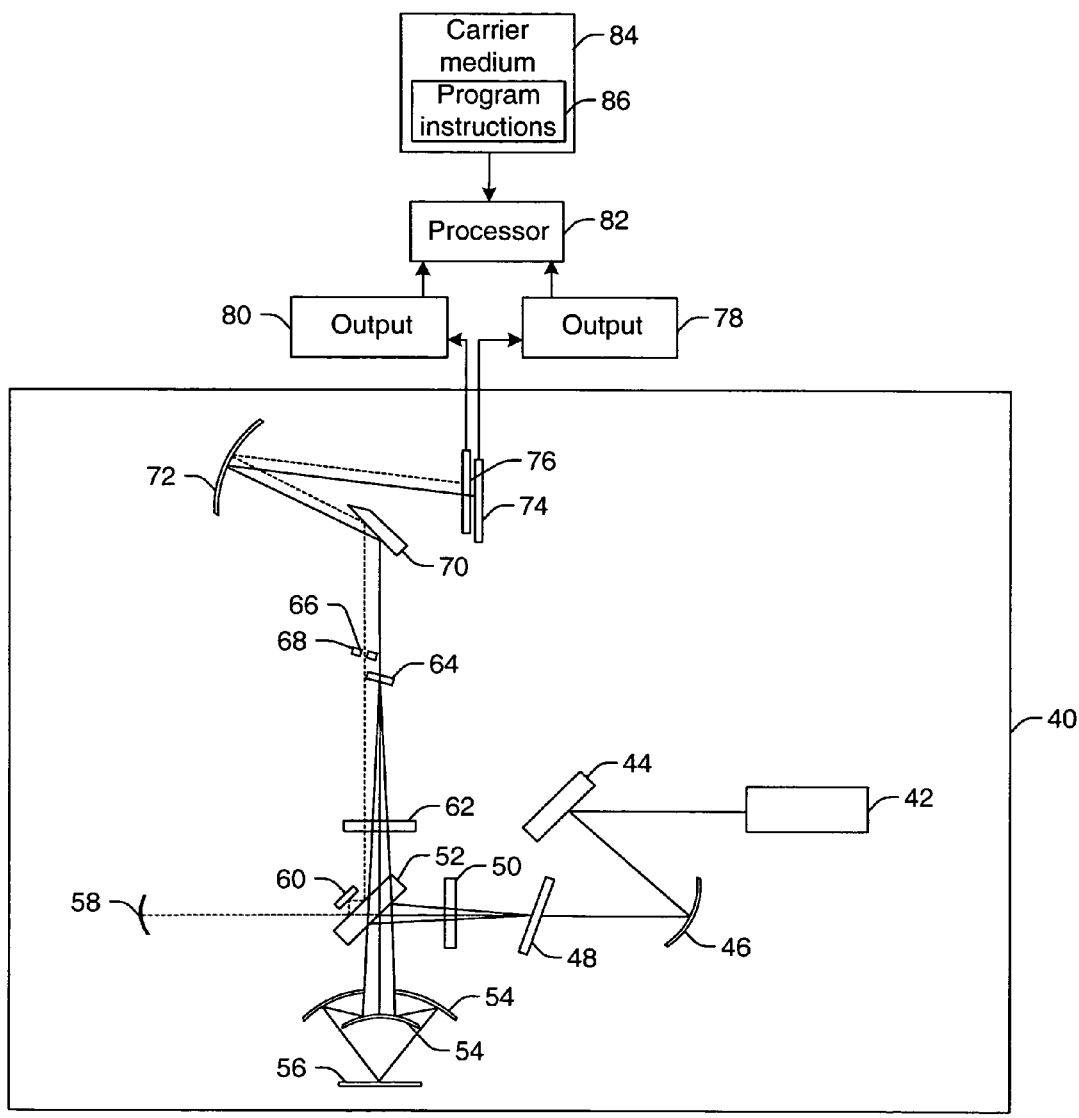
Figure 3:
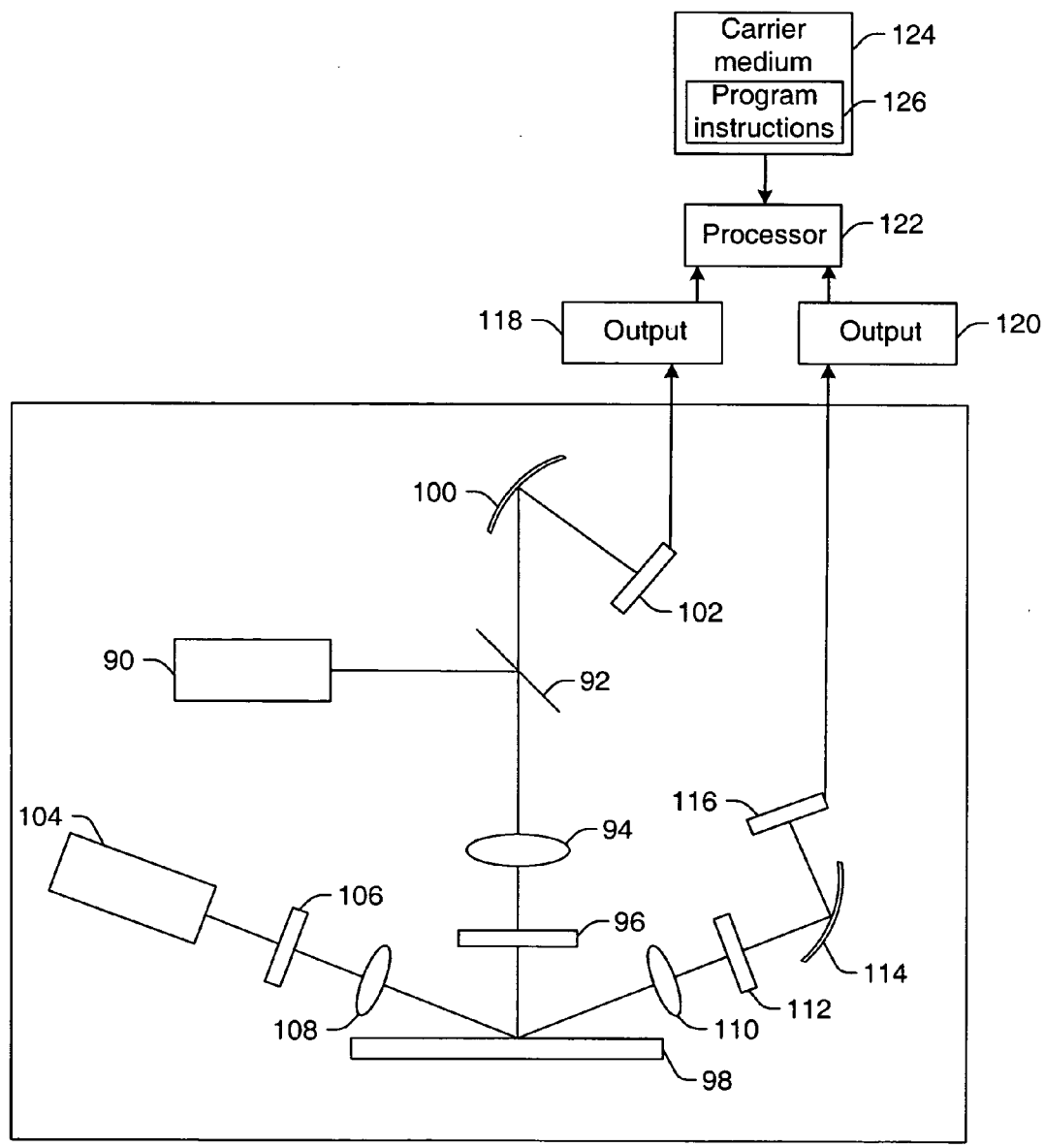

Accordingly, the optical subsystem may have many different configurations. For example, the optical subsystem may be configured as a spectroscopic ellipsometer, a multi-angle laser ellipsometer, a polarimeter, and a polarized reflectometer. Several different embodiments of an optical subsystem are illustrated in FIGS. 1-3. However, these embodiments are merely presented as examples of suitable optical subsystem configurations, and it is noted that the optical subsystem may have any optical configuration known in the art that is capable of measuring change in polarization of light due to the interaction of the light with patterned structures on a specimen. For example, optical subsystems included in tools such as the SpectraCD 100, ASET-F5x, and SpectraFx 100, which are commercially available from KLA-Tencor, San Jose, Calif., may be included in the systems described herein and used to perform the measurements described herein.

Optical subsystem 10 shown in FIG. 1 is configured as a spectroscopic ellipsometer. For example, light from broadband light source 11 such as a Xenon lamp or any other suitable light source is directed to polarizer 12. In one embodiment, the polarizer may be a Rochon prism. The polarizer may be rotated during measurements such that the optical subsystem functions as a rotating polarizer spectroscopic ellipsometer. Alternatively, the position of the polarizer may be constant throughout the measurements. In some embodiments, the light may be directed from the broadband light source to the polarizer by one or more optic fibers (not shown). Focusing mirror 14 reflects the light passed through the polarizer and focuses the beam to a spot on wafer surface 16. In some instances, the beam may be focused to a relatively small spot area (40 µm×40 µm, for instance) on the wafer. However, the spot area of the beam on the wafer may vary depending on, for example, the characteristics of the focusing mirror. Preferably, the optical subsystem and/or wafer 16 is positioned such that the optical subsystem illuminates patterned structures formed on the specimen. Due to the size of the spot area of the illumination beam and the size of the patterned structures, the optical subsystem will typically illuminate multiple patterned structures substantially simultaneously. The structures that are illuminated simultaneously may all have the same general configuration (e.g., as in an array of patterned structures).

The incident beam is reflected by the wafer, and the reflected light beam is collected by collection mirror 18. The beam is then directed to analyzer 20 via folding mirror 22 and finally arrives at the entrance slit of spectrometer 24. Spectrometer 24 generates output 26 in response to the detected light at the different wavelengths. The output of the spectrometer will vary depending on the change in polarization of the light reflected from the wafer. In addition, as described further herein, the change in polarization caused by the patterned structures will vary depending on the amount of stress-induced birefringence present in the patterned structures. As such, the output contains stress-induced birefringence measurements of the patterned structures formed on the specimen.

Optical subsystem 10 may also include other components that are not shown in FIG. 1 (for the sake of clarity) such as a stage configured to support the wafer, a focusing subsystem, etc. In addition, the configuration of the components of the optical subsystem may vary depending on, for example, the type of material that is formed in the patterned structures that are being measured. For instance, since the optical subsystem is performing stress-induced birefringence measurements of the material, the material of the patterned structures should be at least partially transparent to at least one wavelength of illumination of the optical subsystem. In this manner, the wavelength of illumination of the optical subsystem may vary depending on the material that is being measured. For example, in some instances, the optical subsystem may be configured to measure the stress-induced birefringence at one or more infrared wavelengths. In one such example, if the stressed material to be measured is silicon, then the optical subsystem may be configured as an infrared spectroscopic ellipsometer.

The system also includes processor 28. Processor 28 is coupled to the optical subsystem. For example, processor 28 may be coupled to spectrometer 24 of the optical subsystem such that the processor may receive output 26 from spectrometer 24. In one such example, spectrometer 24 may be coupled to processor 28 by a transmission medium (not shown). The transmission medium may include "wired" and "wireless" portions. The processor may also be coupled to other components of the optical subsystem in a similar or different manner such that the processor can receive information about parameters of the components and can send one or more control signals to the components.

The processor is configured to determine stress in a material of patterned structures on wafer 16 using the stress-induced birefringence measurements performed by the optical subsystem. For example, measuring the stress-induced birefringence includes measuring the change in the polarization of light due to the patterned structures. The polarization of the light reflected by the specimen is changed by the presence of the patterned structures even without stress. Any stress in the transparent part of the structures leads to stress-induced birefringence in the material. As the light passes through this stressed material, its polarization is additionally affected. Therefore, the ellipsometric method used by optical subsystem 10 and the methods used by other optical subsystems described herein measure the change in polarization due to the combination of the pattern and the stress.

The amount of polarization change due to stress can be estimated by a simple calculation. For example, the equation for the angular retardance, $\Delta$, from stress-induced birefringence is: $\Delta = 2\pi C \sigma T/\lambda$, where $C$ is the stress-optical coefficient, $\sigma$ is the stress, $T$ is the optical path length through the material, and $\lambda$ is the wavelength of the light. The stress-optical coefficient of silicon dioxide is $2.4e{-}12$ $Pa^{-1}$. Assuming a typical stress of 100 MPa, a path length of 1 µm, and a wavelength of 400 nm, in this case, there will be about 0.004 radians of retardation due to stress. Modern spectroscopic ellipsometers are capable of measuring these values of retardation and even lower values. Therefore, these optical subsystems will have adequate sensitivity for the measurements described herein.

A mathematical model can be used by processor 28 to predict the stress in the patterned structures based on parameters of the geometry of the patterned structures and the polarization change. For example, optical modeling of patterned arrays (which in the past have not accounted for stress) is a topic of much current work. Examples of such optical models are illustrated in U.S. Pat. No. 6,590,656 to Xu et al., which is incorporated by reference as if fully set forth herein. The processor may be configured to use such a model or any other appropriate model known in the art to determine one or more geometrical parameters of the patterned structures using output generated by the optical subsystem. The geometrical parameters may include, for example, height, width, pitch, side wall angle, and the like. Parameters of the model are varied until the predicted polarization change matches the data from the optical subsystem. The stress parameter used in the model is then a good estimate of the actual stress in the patterned structures. In this manner, the processor may determine one or more geometrical parameters and the stress in patterned structures on a specimen substantially simultaneously using a model describing the effects of variations in the one or more geometrical parameters and the stress on polarization change in light detected by the optical subsystem.

Stress in the patterned structures will also affect the optical measurements of the geometrical parameters. For example, the stress-induced birefringence may affect any optical measurements (such as ellipsometric measurements) of the patterned structures, which will then affect any characteristics of the patterned structures determined from the optical measurements. In addition, if the changes that the stress-induced birefringence causes in the optical measurements are not accounted for, then the characteristics determined from these optical measurements will be at least somewhat inaccurate. As such, the optical model that is used by the processor can be modified such that the stress that is measured in the patterned structures is used to correct the optical measurements of the patterned structures and/or the geometrical parameters of the patterned structures. Therefore, the systems and methods described herein may determine the geometrical parameters (and optionally other characteristics) of the patterned structures with greater accuracy than other systems and methods available for measuring characteristics of patterned structures.

Since the optical subsystem will normally illuminate multiple patterned structures during a measurement, the stress that is measured may be an average stress in the material of more than one of the patterned structures. In another embodiment, the stress may be calculated as a stress distribution in the material of the patterned structures. In such an embodiment, the processor may be configured to determine the stress distribution in the material using the stress-induced birefringence measurements and a finite element modeling (FEM) method. In particular, the stress distribution can be modeled using a FEM, and the FEM can be combined with the optical model described above to produce a more accurate model to analyze the data.

The processor may also be configured to perform any other suitable or advantageous functions. For example, the processor may be configured to monitor one or more processes used to fabricate the patterned structures. In one particular example, the processor may be configured to monitor one or more processes used to fabricate the patterned structures using the stress measured in the patterned structures. The processor may monitor the processes to determine if the processes are out-of-spec. The processes may include front end of line (FEOL) processes or back end of line (BEOL) processes. In some embodiments, the processor may also or alternatively be configured to control one or more processes used to fabricate the patterned structures using, for example, a feedback control technique. In additional embodiments, the processor may be configured to control one or more processes that will be used to fabricate the specimen using, for example, a feedforward control technique. The processes may be controlled using the stress measurements and/or in response to the monitoring of the processes.

As shown in FIG. 1, the system may also include program instructions 32 that are executable on processor 28 to determine stress in a material of the patterned structures using the stress-induced birefringence measurements. Program instructions implementing methods such as those described herein may be transmitted over or stored on carrier medium 30. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The optical subsystem shown in FIG. 1 may be modified such that the optical subsystem has other ellipsometer configurations. For example, broadband light source 11 may be replaced with a laser light source. In addition, various components of the ellipsometer such as polarizer 12, focusing mirror 14, and collection mirror 18 may be configured such that the positions of these components may be varied. In particular, the position of these and other components of the ellipsometer may be varied such that measurements may be performed on the specimen at multiple angles. In this manner, the optical subsystem may be configured as a multi-angle laser ellipsometer. Many other ellipsometer configurations are known in the art and the optical subsystem shown in FIG. 1 may have any such optical configuration. For example, the optical subsystem may be configured as described in U.S. Pat. No. 6,590,656 to Xu et al.

Another example of an optical subsystem that may be included in the systems described herein is illustrated in FIG. 2. Optical subsystem 40 is configured as a polarimeter. In this example, the optical subsystem includes light source 42. The light source may include a broadband light source such as a Xenon arc lamp or any other suitable light source known in the art. Light generated by the light source is directed to flat mirror 44, which directs the light to concave mirror 46. Concave mirror 46 directs the light to aperture mirror 48, which may provide some focus control for the optical subsystem.

Light emerging from aperture mirror 48 passes through polarizer 50. Polarizer 50 may include any suitable polarizer known in the art. The polarizer may be static (i.e., non-rotating) in this example. The polarizer is used to alter the polarization of the light to some known polarization. In an alternative, flat mirror 44, concave mirror 46, and aperture mirror 48 may be eliminated from the optical subsystem, and the light source may direct the light directly to the polarizer. In another alternative example, beamsplitter 52 may be configured to alter the polarization of the light to a selected polarization. In this example, the beamsplitter may function as the polarizer, and the optical subsystem may not include polarizer 50.

Beamsplitter 52 directs a portion of the light to objective 54. Objective 54 is shown to be a reflective objective. However, it is to be understood that the objective may alternatively be a refractive objective. Objective 54 focuses the light having the selected polarization on specimen 56, which may be supported on an appropriate stage (not shown). The light may have a spot size that is larger than the patterned structures on the specimen. As such, the optical subsystem may illuminate multiple patterned structures substantially simultaneously.

The portion of the light that is transmitted by beamsplitter 52 may be directed to concave mirror 58. This portion of the light may be used as a reference light beam, as described further herein, and is differentiated from the sample light beam in FIG. 2 in that the reference light beam is indicated by a dotted line. Concave mirror 58 is configured to direct the reference light beam to the back surface of beamsplitter 52 such that the reference light beam is reflected from the back surface of the beamsplitter to fold mirror 60. Fold mirror 60 directs the reference light beam again to the back surface of the beamsplitter such that the reference light reflected again by the beamsplitter is properly aligned with other components of the detection portion of the optical subsystem.

Light reflected from the specimen including light that interacted with the patterned structures on the specimen is collected by objective 54. The collected light passes through beamsplitter 52 and through analyzer 62. The reference light reflected from the beamsplitter also passes through analyzer 62. Analyzer 62, like polarizer 50, may be stationary (i.e., non-rotating). However, in other examples, the analyzer or the polarizer may be rotated while the other polarizing component is stationary. Analyzer 62 is configured to analyze the light modified by the specimen (e.g., the change in the polarization of the light due to the patterned structures on the specimen) and collected by objective 54 according to a fixed plane of polarization. In a similar manner, the analyzer may analyze the reference light beam.

After passing through analyzer 62, the light reflected from the specimen passes through a sample spectrometer pinhole (not shown) in sample plate 64. In addition, the reference light beam, after passing through analyzer 62, passes through reference spectrometer pinhole 66 in reference plate 68. The light beams that pass through the sample spectrometer pinhole and the reference spectrometer pinhole are then reflected by fold mirror 70 to diffraction grating 72. Diffraction grating 72 may be a concave holographic grating or any other suitable diffraction grating known in the art. The resulting first order diffraction beam of the light returned from the specimen is collected by sample linear photodiode array 74. Photodiode array 74 measures the specimen polarimetric spectrum. The resulting first order diffraction beam of the reference light beam is collected by reference linear photodiode array 76. Photodiode array 76 measures the reference polarimetric spectrum. The optical subsystem shown in FIG. 2 may be further configured as described in U.S. Pat. No. 6,611,330 to Lee et al., which is incorporated by reference as if fully set forth herein.

Photodiode arrays 74 and 76 generate output 78 and 80, respectively, which contain the detected polarimetric spectra. Output 78 and 80 may be sent to processor 82, which may be coupled to photodiode arrays 74 and 76 as described above (e.g., via transmission media). The processor may use the output to determine the stress in a material of the patterned structures using the stress-induced birefringence measurements (e.g., the measurements that indicate how the material in the patterned structures alters the polarization of light). The processor may determine the stress in the material as described above.

In addition, the processor may use the output to determine a relative reflectance spectrum. For example, the relative reflectance spectrum can be obtained by dividing the intensity of the light returned from the specimen at each wavelength by the reference light beam intensity at the corresponding wavelengths. In this manner, the optical subsystem illustrated in FIG. 2 may be configured not only as a polarimeter, but also as a polarized reflectometer. In addition, the optical subsystem is further configured as a polarized spectroscopic reflectometer. The processor may be further configured as described above. In addition, the system shown in FIG. 2 may be further configured as described above. For example, the system includes carrier medium 84 and program instructions 86, which may be configured as described above.

FIG. 3 illustrates yet another embodiment of an optical subsystem that may be included in the systems described herein and used to measure stress-induced birefringence in patterned structures formed on the specimen. This optical subsystem is configured as a polarimeter. In particular, this optical subsystem is configured as a normal incidence polarimeter and an oblique incidence polarimeter. One or both of the polarimeters may be single wavelength polarimeters. Alternatively, one or both of the polarimeters may be spectroscopic polarimeters.

In particular, the optical subsystem shown in FIG. 3 includes broadband light source 90, beamsplitter 92, which directs the light beam towards objective lens 94. The light beam passes through objective lens 94 and is then polarized by polarizer 96, which is rotatable. The polarized light beam is incident on and reflected by specimen 98. The optical subsystem and/or the specimen may be positioned such that the polarized light beam is incident on patterned structures on the specimen. In addition, the optical subsystem may illuminate multiple patterned structures substantially simultaneously. The reflected light is again transmitted through polarizer 96 and objective lens 94. The light beam passes through beamsplitter 92 and is focused into the slit (not shown) of a spectrograph that includes diffraction grating 100 and multichannel array detector 102.

The oblique incidence polarimeter includes light source 104, polarization state generator (PSG) 106, lens 108 (or a series of lenses) before specimen 98, another lens 110 (or a series of lenses) after specimen 98, polarization state detector (PSD) 112, diffraction grating 114, and multichannel array detector 116, which analyzes the polarization state after reflection, from which the ellipsometry angles can be obtained. Like the normal incidence polarimeter, the oblique incidence polarimeter may illuminate multiple patterned structures substantially simultaneously. PSG 106 can be a linear polarizer with its transmission axis at an angle from the plane of incidence, where PSD 112 may be either a rotating compensator and fixed analyzer, a rotating analyzer, a photoelastic modulator followed by an analyzer, or any other optical component that creates an intensity modulation as a function of known system parameters such as position of the compensator fast axis or analyzer transmission axis in the case of a rotating compensator or rotating analyzer system, respectively, or effective phase retardance as a function of time in the case of a photoelastic modulator. The ellipsometry angles can then be extracted from the mathematical analysis of the modulated intensity using Jones matrix or Mueller matrix formulations. This optical subsystem may be further configured as described in U.S. Pat. No. 6,713,753 to Rovira et al., which is incorporated by reference as if fully set forth herein.

Multichannel array detectors 102 and 116 generate output 118 and 120, respectively, containing the detected polarimetric data or spectra. Output 118 and 120 may be sent to processor 122, which may be coupled to multichannel array detectors 102 and 116 as described above (e.g., via transmission media). The processor may use the output to determine the stress in a material of the patterned structures using the stress-induced birefringence measurements (e.g., the measurements that indicate how the material in the patterned structures alters the polarization of light). The processor may determine the stress in the material as described above. The processor may be further configured as described above. In addition, the system shown in FIG. 3 may be further configured as described above. For example, the system may include carrier medium 124 and program instructions 126, which may be configured as described above.

The systems shown in FIGS. 1-3 may also include one or more additional optical subsystems. For example, one system may include the optical subsystems shown in FIGS. 1 and 2. In another example, the systems may include another optical subsystem such as a scatterometer that is configured to perform additional measurements of the patterned structures and/or the specimen. The additional optical subsystem(s) may include one or more optical components of the optical subsystems shown in FIGS. 1-3 (such as a common light source). In addition, the additional optical subsystem(s) may include one or more other components of the systems of FIGS. 1-3 (such as a common processor, a common power source, a common specimen handler, etc.). The systems shown in FIGS. 1-3 may also include one or more additional non-optical subsystems. For example, the systems shown in FIGS. 1-3 may include an electron beam tool such as a critical dimension scanning electron microscope (CD SEM). Such additional optical and/or non-optical subsystem(s) may be advantageously included in the system, and the measurements performed by the additional subsystem(s) may be used to confirm and/or correct the geometrical parameters determined from the optical subsystem measurements. For instance, measurements performed by a CD SEM may be used as input to the optical models described above.

The systems shown in FIGS. 1-3 may also include one or more processing subsystems. For example, the systems shown in FIGS. 1-3 may include a semiconductor fabrication process tool. In another example, the systems shown in FIGS. 1-3 may include a repair tool that may be used to repair any damaged patterned structures or specimen damage. In a further example, the systems shown in FIGS. 1-3 may be coupled to other metrology and/or inspection systems such as a review tool. The optical subsystems shown in FIGS. 1-3 may be coupled to a semiconductor fabrication tool, a repair tool, and/or a review tool physically, for example, by a common power source, a common stage, a common specimen handler, etc. Alternatively, the optical subsystems may be coupled to such tools "virtually" through, for example, a transmission medium, a processor, a fab database, etc. The optical subsystems and the tool may also be coupled in any other suitable manner.

The systems described above have many advantages over other systems that can measure stress in a material such as x-ray diffraction (XRD) and Raman spectroscopy. For example, the systems described above can measure more materials than XRD and Raman spectroscopy can measure. In particular, unlike XRD, the systems described herein can be used to measure crystalline and non-crystalline materials. In addition, unlike Raman spectroscopy, the systems described herein can be used to measure silicon as well as materials other than silicon. In addition, the systems described herein will have better signal-to-noise ratios and higher throughput than both XRD systems and Raman spectroscopy systems.

Figure 4:
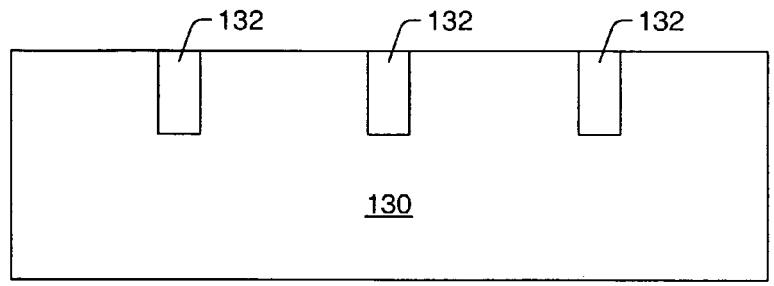
FIGS. 4 and 5 are schematic diagrams illustrating cross-sectional views of different examples of patterned structures that can be measured using the systems and methods described herein.
Figure 5:
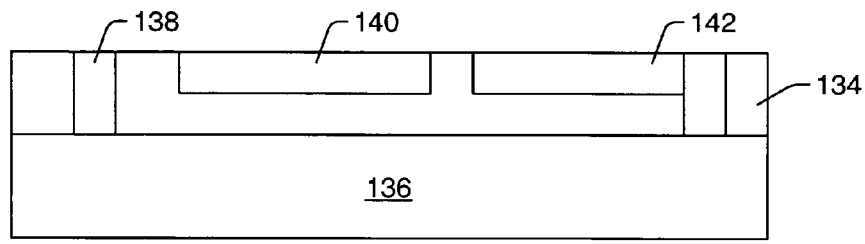

Examples of patterned structures that can be measured using the systems and methods described herein are illustrated in FIGS. 4 and 5. FIG. 4 illustrates one example of shallow trench isolation (STI) structures. In particular, trenches 132 are etched in silicon layer 130. The silicon layer may be, for example, a silicon substrate. Alternatively, the silicon layer may be a silicon layer formed on a substrate. Although three trenches are shown formed in the silicon layer, it is to be understood that the number of the trenches and other characteristics of the trenches will vary depending on, for example, the characteristics of the devices being formed. The dielectric material may be formed in the trenches, for example, by depositing the dielectric material on the substrate and then planarizing the dielectric. Examples of a suitable dielectric material include silicon dioxide and silicon nitride. In addition, multiple dielectric materials may be formed in the trenches.

In this example, the STI structures including the parallel trenches filled with a dielectric can be measured with an optical subsystem configured as, for example, a spectroscopic ellipsometer having a plane of incidence that is substantially normal to the trenches. The resulting signal can be compared by the processor to a theoretically computed signal based on initial guesses of the parameters of the geometry of the dielectric material in the trenches and the average stress in the dielectric material. The geometrical parameters and the average stress can be varied in the model by the processor until a best fit between the model and the data is obtained.

FIG. 5 illustrates one example of copper interconnect structures. In this example, dielectric layer 134 is formed on layer 136 that contains device structures (not shown) such as transistors and/or additional interconnects. The copper interconnect structures may serve as electrical connections between different device structures. Copper interconnect structures 138, 140, and 142 are formed in dielectric layer 134. In this example, copper interconnect structure 138 is a hole, copper interconnect structure 140 is a trench, and copper interconnect structure 142 is a combination of a hole and a trench. Although different types of copper interconnect structures are shown formed in the dielectric layer, it is to be understood that the copper interconnect structures formed in the dielectric layer may all have the same configuration. In addition, it is to be understood that the number of the copper interconnect structures and other characteristics of the copper interconnect structures formed in the dielectric layer will vary depending on the characteristics of the device being formed.

The two types of patterned structures illustrated in FIGS. 4 and 5 are only two examples of the many different types of patterned structures and materials for which the systems described herein can be used to perform stress measurements. Being able to perform stress measurements directly on such patterned structures as described herein is particularly advantageous since these structures are particularly susceptible to damage caused by stress in the material of the patterned structures. For example, high levels of stress can build up in the STI structures due to the dissimilar materials and can effect the electrical performance of the transistor and can even lead to cracking in the corners of the trenches. Stress can also build up in copper interconnect structures and cause problems such as void formation in the copper, which can lead to complete breaks in the copper lines thereby forming open circuits. Accordingly, stress measurements for STI and copper interconnect structures may be particularly important, and yet previously no systems exist that can be used to make such measurements. Therefore, the systems described herein provide significant advantages for semiconductor manufacturing. For example, the systems described herein can be used to improve the performance and reliability of semiconductor devices such as integrated circuits and to increase the yield in semiconductor fabrication.

Figure 6:
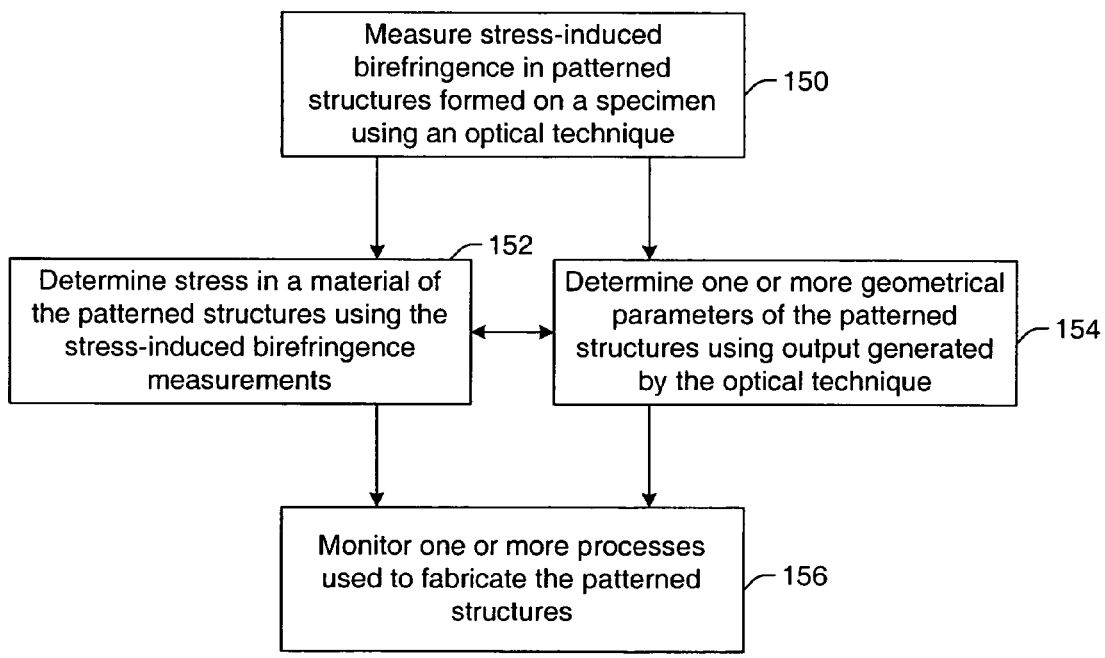
FIG. 6 is a flow chart illustrating one embodiment of a method for measuring stress in a specimen.

FIG. 6 illustrates one embodiment of a method for measuring stress in a specimen. As shown in step 150 of FIG. 6, the method includes measuring stress-induced birefringence in patterned structures formed on a specimen using an optical technique. The optical technique may include spectroscopic ellipsometry, multi-angle laser ellipsometry, polarimetry, polarized reflectometry, or some combination thereof. Therefore, the measuring step may be performed using one or more of the optical subsystems described herein.

The patterned structures may include those described herein including, for example, trenches filled with a dielectric material (e.g., STI structures) and copper interconnect structures. The patterned structures may also include any other patterned structures known in the art. The material of the patterned structures is preferably at least partially transparent to at least one wavelength of light used by the optical technique. Therefore, the wavelength(s) used by the optical technique may be selected as described above based on the material in the patterned structures. In one example, the stress-induced birefringence measurements may be performed at one or more infrared wavelengths. Such measurements may be appropriate for materials such as silicon.

The method also includes determining stress in a material of the patterned structures using the stress-induced birefringence measurements, as shown in step 152 of FIG. 6. The stress in the material may be determined as described above. In addition, a processor and/or program instructions as described above may be used to determine the stress in the material. The stress may be an average stress in the material of more than one of the patterned structures. Alternatively, the stress may be a stress distribution in the material. In such an embodiment, determining the stress may include determining the stress distribution in the material using the stress-induced birefringence measurements and a finite element modeling method.

In some embodiments, the method may include determining one or more geometrical parameters of the patterned structures using output generated by the optical technique, as shown in step 154. The one or more geometrical parameters of the patterned structures may be determined as described above, for example, using an optical model. In addition, the stress and the geometrical parameter(s) may be determined substantially simultaneously using a model describing effects of variation in the one or more geometrical parameters and the stress on polarization change in light used by the optical technique.

In another embodiment, the method may include monitoring one or more processes used to fabricate the patterned structures, as shown in step 156. For example, the stress in the patterned structures and/or the geometrical parameters of the patterned structures may be used to determine if a process is "out-of-spec." In a further embodiment, the method may include controlling one or more processes used to fabricate the patterned structures using, for example, a feedback control technique. In an additional embodiment, the method may include controlling one or more processes that will be used to fabricate the specimen using, for example, a feedforward control technique. The one or more processes that are monitored and/or controlled may include FEOL processes or BEOL processes. Each of the embodiments of the method described above may include any other step(s) described herein.

Further modifications and alternative embodiments of various aspects of the invention may be apparent to those skilled in the art in view of this description. For example, systems and methods for measuring stress in a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to measure stress in a specimen, comprising:
    an optical subsystem configured to measure stress-induced birefringence in patterned structures formed on the specimen; and
    a processor coupled to the optical subsystem, wherein the processor is configured to determine stress in a material of the patterned structures using the stress-induced birefringence measurements, wherein the processor is further configured to determine one or more geometrical parameters of the patterned structures using output generated by the optical subsystem, and wherein the processor is further configured to determine the one or more geometrical parameters and the stress substantially simultaneously using a model describing effects of variations in the one or more geometrical parameters and the stress on polarization change in light detected by the optical subsystem.

2. The system of claim 1, wherein the optical subsystem is configured as a spectroscopic ellipsometer.

3. The system of claim 1, wherein the optical subsystem is configured as a multi-angle laser ellipsometer.

4. The system of claim 1, wherein the optical subsystem is configured as a polarimeter.

5. The system of claim 1, wherein the optical subsystem is configured as a polarized reflectometer.

6. The system of claim 1, wherein the patterned structures comprise trenches filled with a dielectric material.

7. The system of claim 1, wherein the patterned structures comprise copper interconnect structures.

8. The system of claim 1, wherein the material of the patterned structures is at least partially transparent to at least one wavelength of light of the optical subsystem.

9. The system of claim 1, wherein the optical subsystem is further configured to measure the stress-induced birefringence at one or more infrared wavelengths.

10. The system of claim 1 wherein the processor is further configured to monitor one or more processes used to fabricate the patterned structures, and wherein the one or more processes comprise front end of line processes or back end of line processes.

11. The system of claim 1, wherein the stress comprises an average stress in the material of more than one of the patterned structures.

12. The system of claim 1, wherein the stress comprises a stress distribution in the material, and wherein the processor is further configured to determine the stress distribution in the material using the stress-induced birefringence measurements and a finite element modeling method.

13. A system configured to measure stress in a specimen, comprising:
    an optical subsystem configured to measure stress-induced birefringence in patterned structures formed on the specimen; and
    program instructions executable on a processor to determine stress in a material of the patterned structures using the stress-induced birefringence measurements, to determine one or more geometrical parameters of the patterned structures using output generated by the optical subsystem, and to determine the one or more geometrical parameters and the stress substantially simultaneously using a model describing effects of variations in the one or more geometrical parameters and the stress on polarization change in light detected by the optical subsystem.

14. A method for measuring stress in a specimen, comprising:
   measuring stress-induced birefringence in patterned structures formed on the specimen using an optical technique;
   determining stress in a material of the patterned structures using the stress-induced birefringence measurements; and
   determining one or more geometrical parameters of the patterned structures using output generated by the optical technique, wherein said determining the stress comprises determining the one or more geometrical parameters and the stress substantially simultaneously using a model describing effects of variations in the one or more geometrical parameters and the stress on polarization change in light used by the optical technique.

15. The method of claim 14, wherein the optical technique comprises spectroscopic ellipsometry.

16. The method of claim 14, wherein the optical technique comprises multi-angle laser ellipsometry.

17. The method of claim 14, wherein the optical technique comprises polarimetry.

18. The method of claim 14, wherein the optical technique comprises polarized reflectometry.

19. The method of claim 14, wherein the patterned structures comprise trenches filled with a dielectric material.

20. The method of claim 14, wherein the patterned structures comprise copper interconnect structures.

21. The method of claim 14, wherein the material of the patterned structures is at least partially transparent to at least one wavelength of the light used by the optical technique.

22. The method of claim 14, wherein said measuring comprises measuring the stress-induced birefringence at one or more infrared wavelengths.

23. The method of claim 14, further comprising monitoring one or more processes used to fabricate the patterned structures, wherein the one or more processes comprise front end of line processes or back end of line processes.

24. The method of claim 14, wherein the stress comprises an average stress in the material of more than one of the patterned structures.

25. The method of claim 14, wherein the stress comprises a stress distribution in the material, and wherein said determining the stress further comprises determining the stress distribution in the material using the stress-induced birefringence measurements and a finite element modeling method.

* * * * *